United States Patent
Hughes et al.

(10) Patent No.: US 9,744,068 B2
(45) Date of Patent: Aug. 29, 2017

(54) FOLDABLE, DISPOSABLE, URINE RECEPTACLE

(71) Applicants: Tara Haven Chrysakis, Tarpon Springs, FL (US); Heather Brooke Stamas, Tarpon Springs, FL (US)

(72) Inventors: Halyn Lee Hughes, Palm Harbor, FL (US); Heather Brooke Stamas, Tarpon Springs, FL (US)

(73) Assignees: Tara Haven Chrysakis, Tarpon Springs, FL (US); Heather Brooke Stamas, Tarpon Springs, FL (US)

( * ) Notice: Subject to any disclaimer, the term of this patent is extended or adjusted under 35 U.S.C. 154(b) by 76 days.

(21) Appl. No.: 13/987,134

(22) Filed: Jul. 1, 2013

(65) Prior Publication Data

US 2015/0000027 A1    Jan. 1, 2015

Related U.S. Application Data

(60) Provisional application No. 61/690,575, filed on Jun. 29, 2012.

(51) Int. Cl.
*A47K 11/00*    (2006.01)
*A61F 5/451*    (2006.01)

(52) U.S. Cl.
CPC .............. *A61F 5/451* (2013.01); *A47K 11/00* (2013.01)

(58) Field of Classification Search
CPC ....................................................... A61G 9/006
USPC ............................................... 4/144.1–144.4
See application file for complete search history.

(56) References Cited

U.S. PATENT DOCUMENTS

| | | | | |
|---|---|---|---|---|
| 1,955,385 A * | 4/1934 | Gray | ...................... | B65D 25/16 217/3 FC |
| 2,689,062 A * | 9/1954 | Brown | ..................... | A47F 1/085 206/499 |
| 3,099,017 A * | 7/1963 | Sullivan | ............... | A61B 10/007 4/144.2 |
| 3,200,415 A * | 8/1965 | Breece, Jr. | .............. | A61F 5/451 128/DIG. 24 |
| 3,329,973 A * | 7/1967 | Bobbe | .................... | A47K 11/06 128/DIG. 24 |
| 3,406,690 A * | 10/1968 | Igel | ......................... | A61F 5/451 600/580 |
| 3,475,767 A * | 11/1969 | Friesen | .................. | A61G 9/006 383/116 |
| 3,572,318 A * | 3/1971 | Garland | ............... | A61B 10/007 141/337 |
| 3,739,975 A * | 6/1973 | Davidow | ........... | A47G 19/2227 206/457 |
| 5,065,459 A * | 11/1991 | Tjahaja | ................. | A61F 5/4407 4/144.2 |
| 5,243,712 A * | 9/1993 | Cross | .................... | A61F 5/4556 4/144.2 |

(Continued)

*Primary Examiner* — Lori Baker
(74) *Attorney, Agent, or Firm* — NK Patent Law, PLLC

(57) ABSTRACT

A foldable, expandable, disposable receptacle, capable of collecting excreta without spilling, and containing it in a secure and sanitary fashion until disposal. The receptacle is slim, form-fitting and contoured, allowing the user to stand upright while urinating. The receptacle allows for modest undressing and prevents contact with any surface other than the floor. A receptacle of lightweight, pliable construction providing easy storage and one-handed manipulation.

7 Claims, 12 Drawing Sheets

(56) References Cited

U.S. PATENT DOCUMENTS

| | | | | |
|---|---|---|---|---|
| 5,408,703 | A * | 4/1995 | Cicio | A47K 11/12 4/144.2 |
| D374,281 | S * | 10/1996 | Markles | A47K 11/12 D24/122 |
| 5,605,161 | A * | 2/1997 | Cross | A61B 10/007 4/144.2 |
| D379,225 | S * | 5/1997 | Canahuate | A61F 5/4556 4/144.4 |
| 5,742,948 | A * | 4/1998 | Cicio | A61F 5/4556 141/337 |
| D394,989 | S * | 6/1998 | Block | A61F 5/4556 D7/700 |
| 6,047,414 | A * | 4/2000 | Bailey | A47K 11/02 4/484 |
| D437,051 | S * | 1/2001 | Hernandez-Fumero | A47K 11/02 D24/122 |
| D447,232 | S * | 8/2001 | Hernandez-Fumero | A47K 11/02 D24/122 |
| D449,105 | S * | 10/2001 | Azo | A47K 11/06 D24/122 |
| 6,324,704 | B1 * | 12/2001 | Imo | A47K 11/12 4/144.2 |
| 6,327,716 | B1 * | 12/2001 | Kaus | A61F 5/4556 4/144.4 |
| 6,406,463 | B1 * | 6/2002 | Brown | A61G 9/006 4/144.1 |
| 6,434,757 | B1 * | 8/2002 | Filsouf | A61F 5/4556 4/144.1 |
| 6,460,200 | B1 * | 10/2002 | Mottale | A61F 5/4556 141/331 |
| 6,468,256 | B1 * | 10/2002 | Mishima | A61F 13/4752 604/385.01 |
| 6,493,884 | B1 * | 12/2002 | Muller | A61B 10/007 141/337 |
| 6,569,135 | B1 * | 5/2003 | Mula | A61F 13/471 604/347 |
| D475,901 | S * | 6/2003 | Makino | A61F 13/471 D7/700 |
| 6,719,741 | B2 * | 4/2004 | Ching | A61F 5/4556 604/329 |
| 6,783,826 | B2 * | 8/2004 | Sherrod | A47K 11/105 4/245.6 |
| D495,798 | S * | 9/2004 | Gugliotta | A61F 5/4556 D24/122 |
| D527,101 | S * | 8/2006 | Fernandez | A47K 11/12 D24/122 |
| 7,086,097 | B2 * | 8/2006 | Shin | A47K 11/12 4/144.1 |
| 7,131,149 | B2 * | 11/2006 | Langford | A61F 5/4556 4/144.2 |
| 7,160,256 | B2 * | 1/2007 | Perlhagen | A61B 10/007 600/580 |
| 7,171,699 | B2 * | 2/2007 | Ernest | A47K 11/12 4/144.1 |
| 7,334,273 | B2 | 2/2008 | Thomas | |
| 7,363,661 | B1 | 4/2008 | Myers | |
| D577,434 | S * | 9/2008 | Stebler | A47K 11/12 D24/122 |
| D579,106 | S * | 10/2008 | Gonzalez | A61B 10/007 D24/122 |
| D579,556 | S * | 10/2008 | Stebler | A61F 5/4556 D24/122 |
| 7,435,242 | B2 * | 10/2008 | Levinson | A61B 10/007 4/144.1 |
| D585,970 | S * | 2/2009 | Dereci | A61F 5/4556 D23/302 |
| D587,366 | S * | 2/2009 | Turkat | A61F 5/4556 D24/122 |
| D602,156 | S * | 10/2009 | Young | A61F 5/4556 D24/122 |
| 7,682,347 | B2 * | 3/2010 | Parks | A61F 5/4556 206/210 |
| 7,694,819 | B2 * | 4/2010 | Montakhabi | A61F 5/4556 206/499 |
| D617,895 | S * | 6/2010 | Aguila | A61F 5/4556 D23/309 |
| D619,246 | S * | 7/2010 | Hazeres | A47K 11/06 D24/122 |
| 7,996,926 | B2 * | 8/2011 | Aguila | A47K 11/12 4/144.1 |
| 7,996,930 | B2 * | 8/2011 | Carter | A47K 11/06 220/495.11 |
| D649,239 | S * | 11/2011 | Taravella | A47K 11/06 D24/122 |
| D650,902 | S * | 12/2011 | Lopez, Jr. | A61F 5/4556 D24/122 |
| 8,117,681 | B2 | 2/2012 | Aguila | |
| 8,146,179 | B1 * | 4/2012 | Duque | A61F 5/4556 4/144.1 |
| 8,192,411 | B2 * | 6/2012 | Lund | A61F 5/445 4/114.1 |
| 8,209,786 | B2 | 7/2012 | Aguila | |
| 8,221,367 | B2 * | 7/2012 | Oprandi | A61F 5/4556 4/144.4 |
| 8,337,477 | B2 * | 12/2012 | Parks | A61F 5/4556 604/329 |
| 8,388,585 | B2 * | 3/2013 | Tomes | A61F 13/15 604/329 |
| 8,388,587 | B1 * | 3/2013 | Gmuer | A61F 5/4556 604/347 |
| 8,490,220 | B1 * | 7/2013 | Hajek | A61F 5/4556 4/144.4 |
| 8,510,877 | B2 * | 8/2013 | Helewa | A47K 11/04 4/484 |
| 8,615,824 | B2 * | 12/2013 | Sonderholm | A61B 10/0038 4/144.2 |
| 8,663,181 | B2 * | 3/2014 | Yang | A61F 5/4408 4/144.1 |
| D703,811 | S * | 4/2014 | Ludert | A01K 1/0125 D24/122 |
| 8,697,202 | B2 * | 4/2014 | Levkovitch | A01K 1/0125 428/12 |
| 8,852,171 | B2 * | 10/2014 | Lund | A61F 5/4404 604/327 |
| 8,945,077 | B2 * | 2/2015 | Valenti | A61F 5/4556 604/317 |
| 2001/0034904 | A1 * | 11/2001 | Phillips | A47K 11/06 4/484 |
| 2002/0193762 | A1 * | 12/2002 | Suydam | A61F 5/4556 604/327 |
| 2003/0125181 | A1 * | 7/2003 | Wei | A63H 27/001 493/405 |
| 2003/0150050 | A1 * | 8/2003 | Tanaka | A61F 5/443 4/144.3 |
| 2004/0064112 | A1 | 4/2004 | Sun | |
| 2004/0181862 | A1 * | 9/2004 | Brummer | A61F 5/4556 4/144.4 |
| 2005/0066431 | A1 * | 3/2005 | Liggieri | E03D 9/00 4/300.3 |
| 2006/0150312 | A1 * | 7/2006 | Gara | A47K 11/00 4/483 |
| 2007/0061951 | A1 * | 3/2007 | Snider | A47K 11/12 4/144.2 |
| 2007/0233028 | A1 * | 10/2007 | Roe | A61F 13/42 604/361 |
| 2007/0234471 | A1 * | 10/2007 | Walker | E03D 9/00 4/300.3 |
| 2007/0270716 | A1 * | 11/2007 | Wu | A61B 5/20 600/580 |
| 2008/0034481 | A1 * | 2/2008 | Cheng | A47K 11/12 4/144.3 |
| 2009/0089919 | A1 * | 4/2009 | Rudolph | A61F 5/4556 4/144.4 |
| 2010/0145179 | A1 * | 6/2010 | Lin et al. | 600/393 |
| 2010/0175179 | A1 * | 7/2010 | Hills | A47K 11/06 4/484 |

* cited by examiner

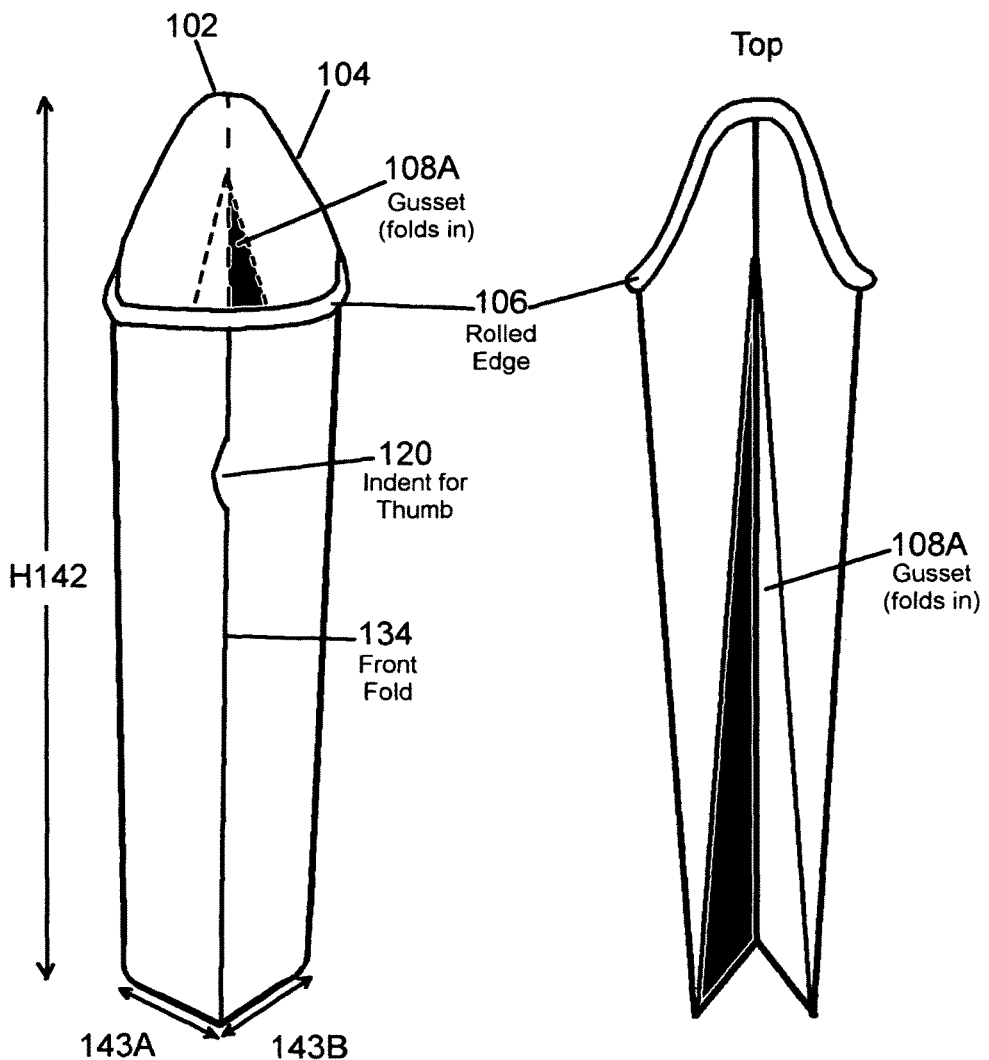

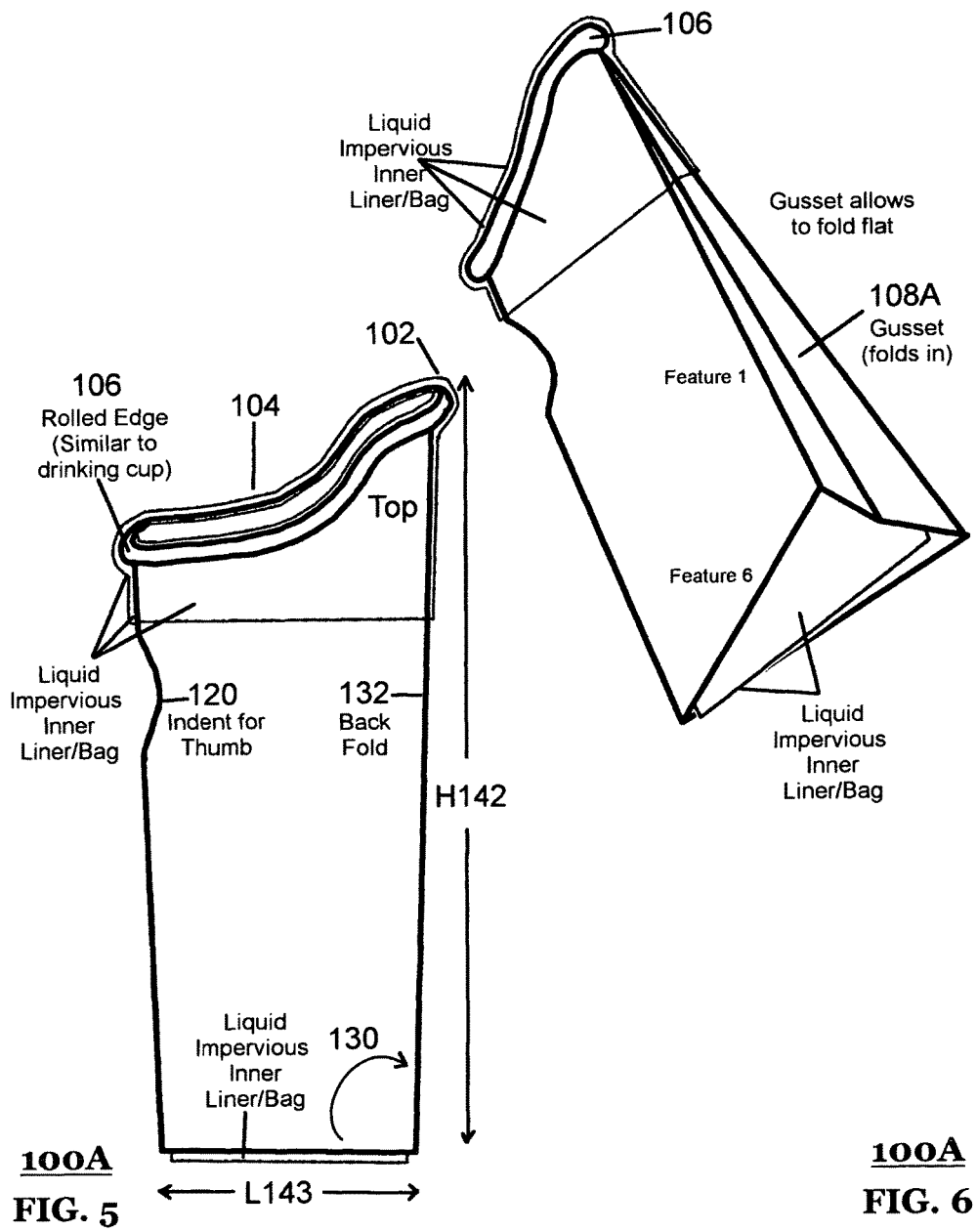

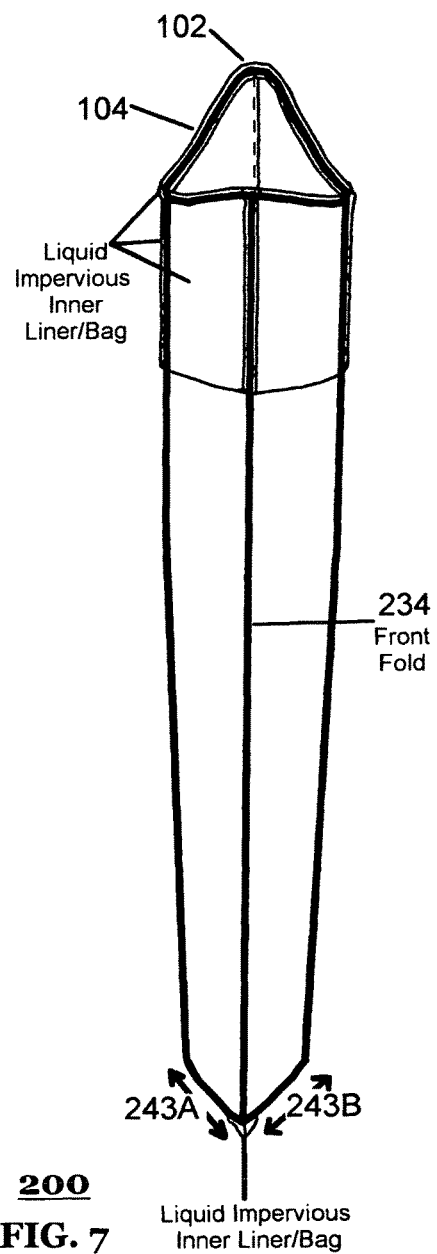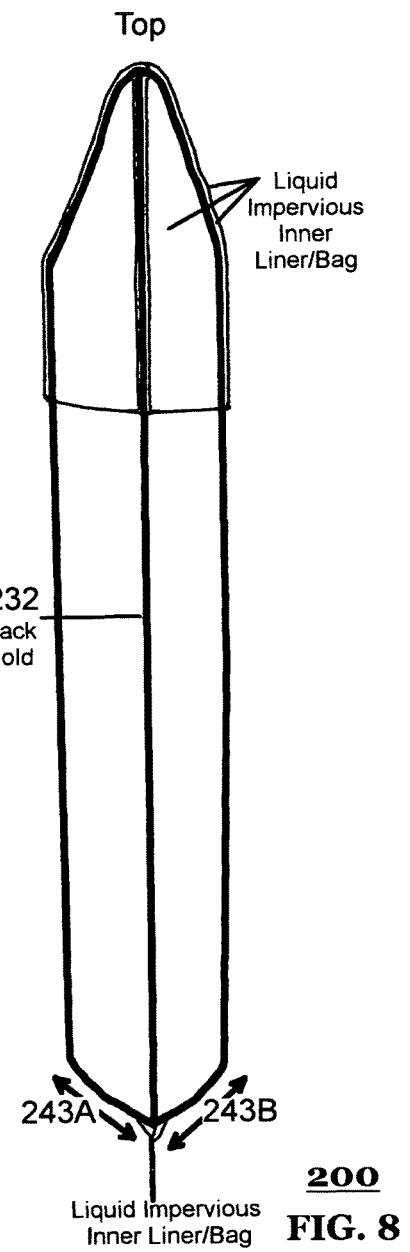

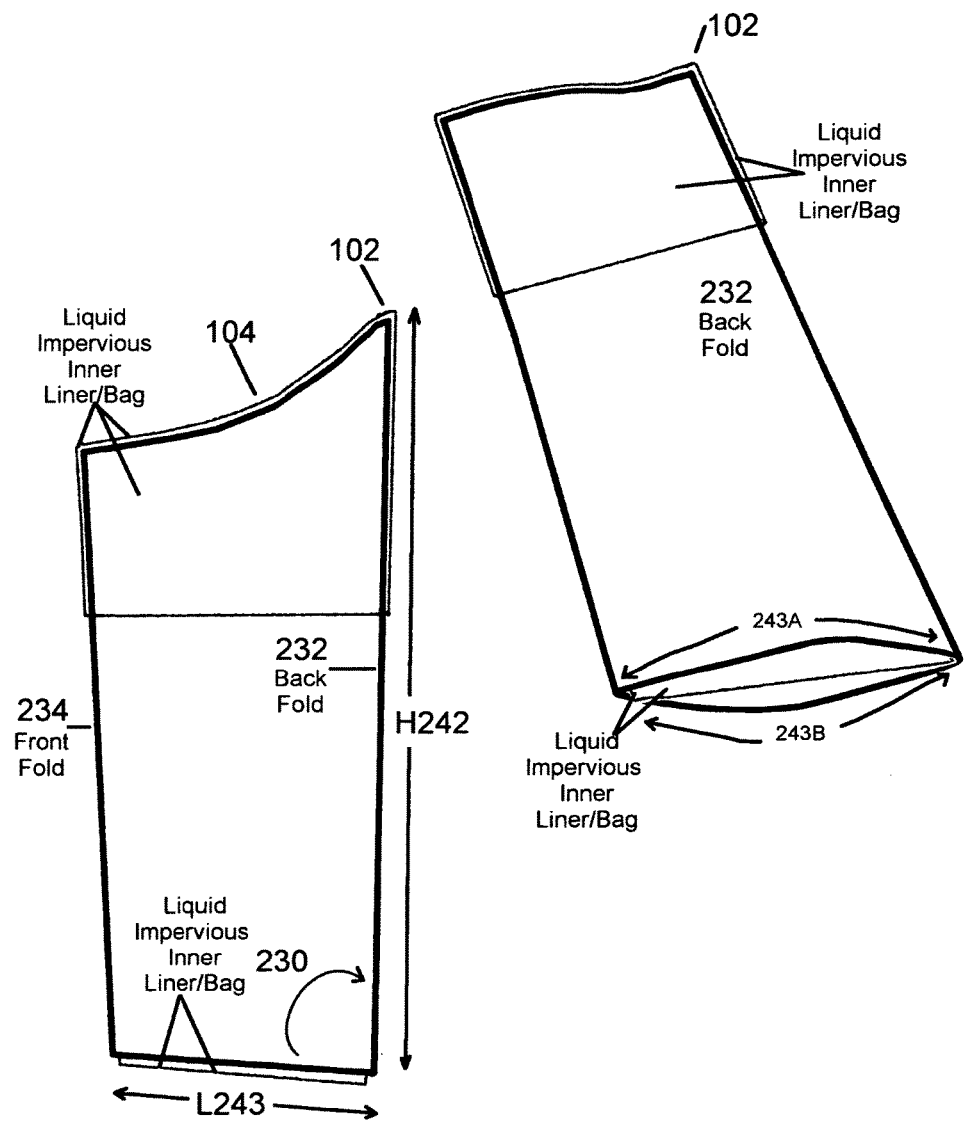

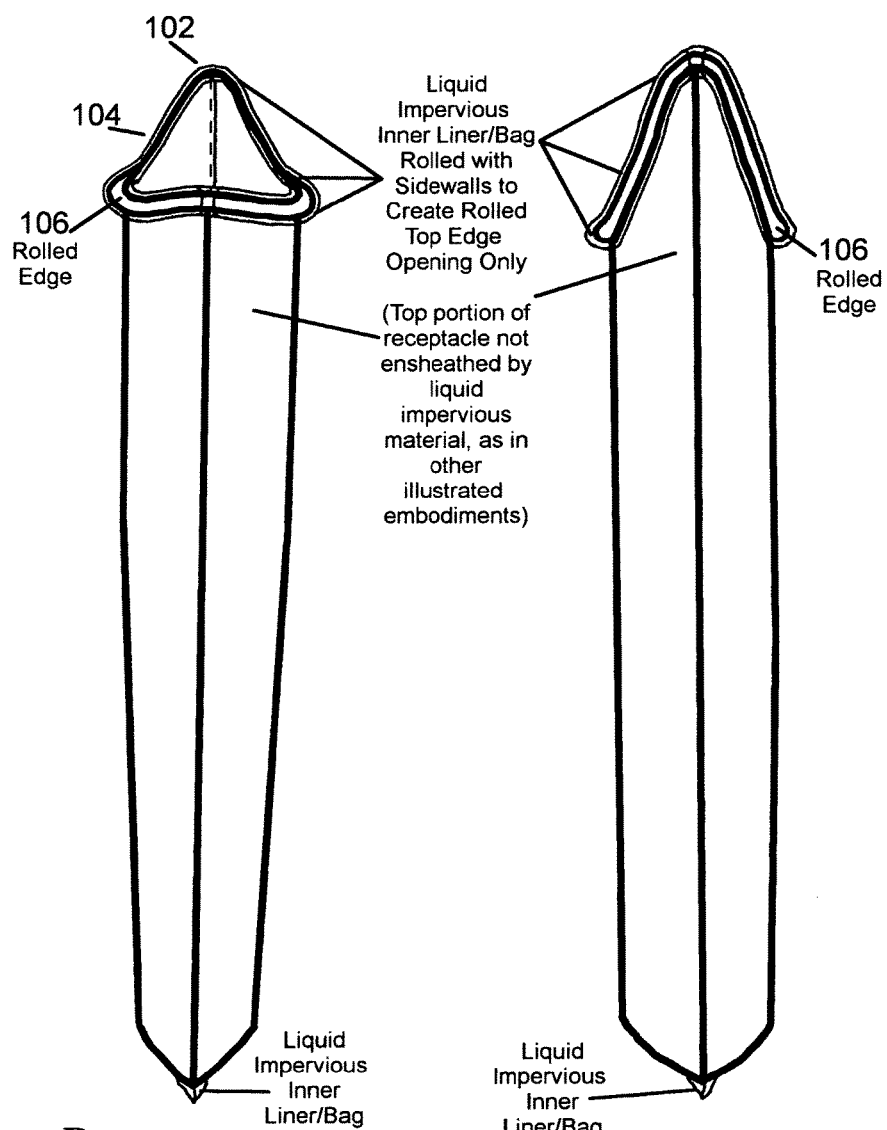

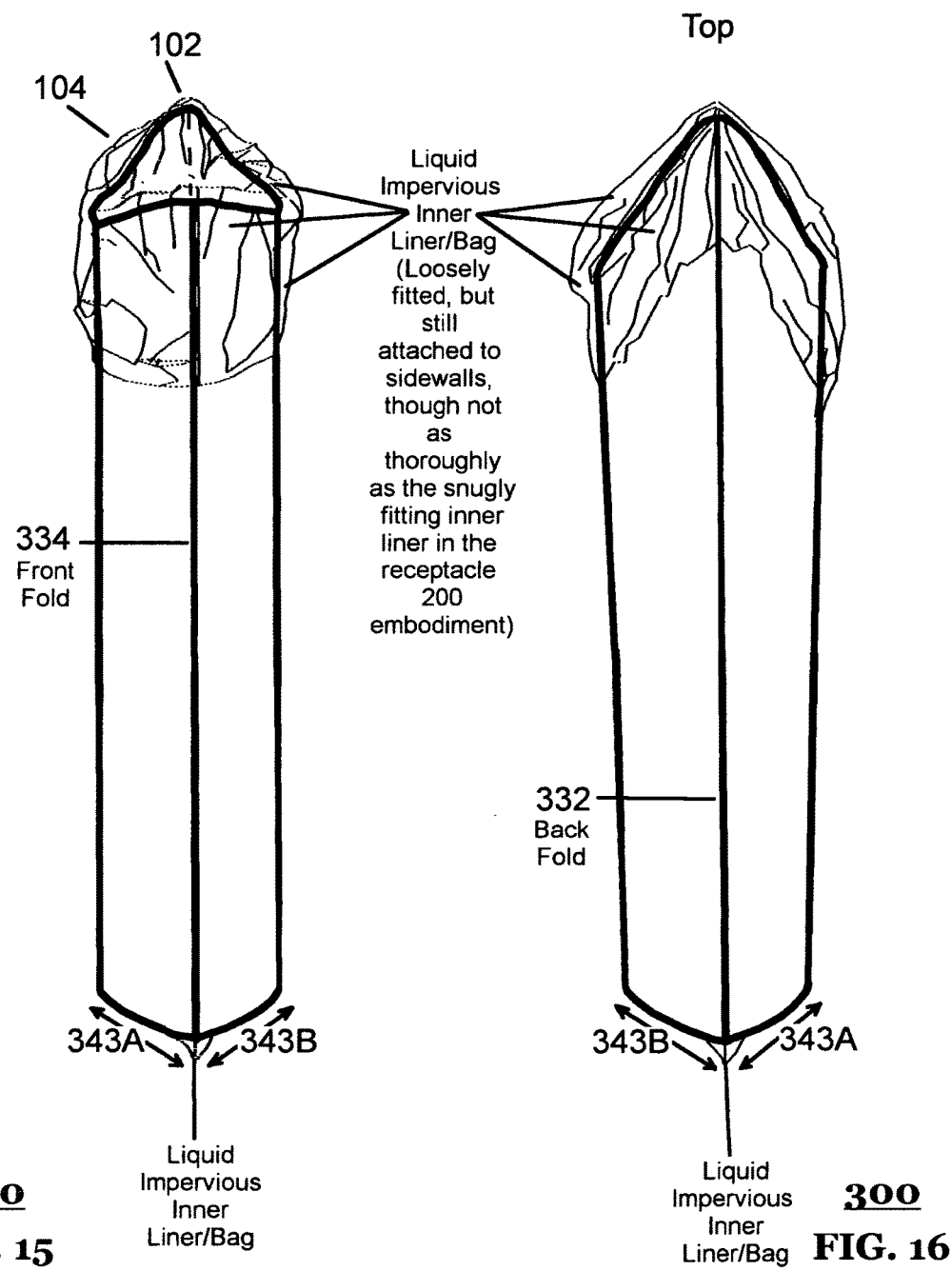

Top View
Tri-Folded
Receptacle
—102

Side View
Tri-Folded
Receptacle
102

Side View
Bi-Folded
Receptacle
102

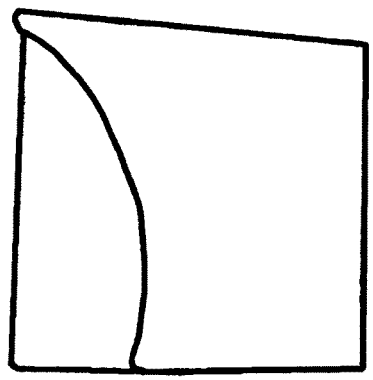

Top View of Receptacle,
(Tri-folded to lay flat)

FIG. 23

Transparent envelope in open
configuration; Tri-folded receptacle
(FIG. 23) shown inserted into
the envelope pocket. Resealable
adhesive strip can be exposed,
ready to be placed back into closed
configuration with receptacle
inside.

Transparent envelope
in closed configuration;
Flap held in place
with resealable
adhesive strip.

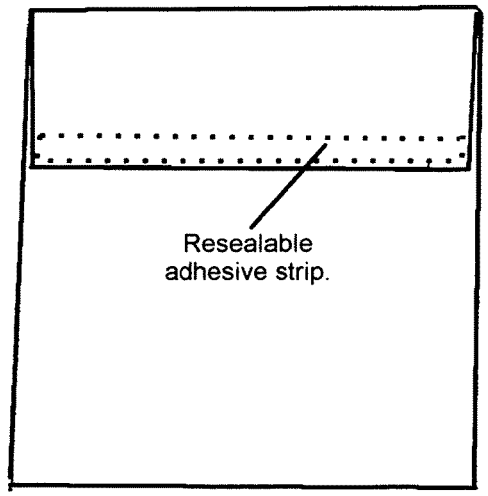

Resealable
adhesive strip.

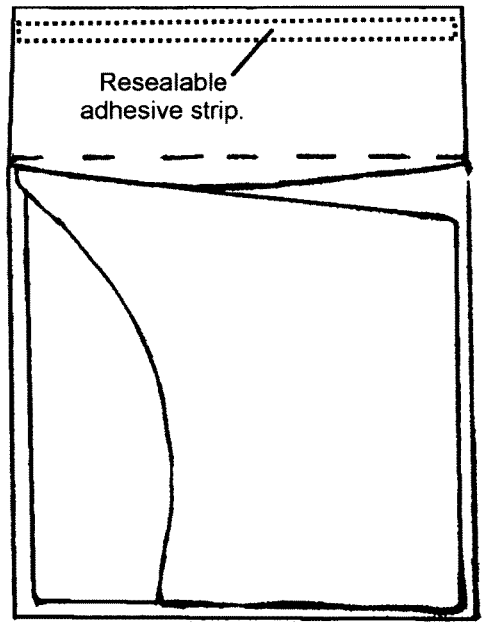

Resealable
adhesive strip.

FIG. 24  FIG. 25

FOLDABLE, DISPOSABLE, URINE RECEPTACLE

This application claims the benefit of U.S. Provisional Application No. 61/690,575 filed Jun. 29, 2012.

FIELD AND BACKGROUND

This invention relates to the field of portable toilet and urinal devices for children and adults, pediatric urinals, and disposable toilet aids for children. There are various products available that aid in a restroom emergency when there are no restrooms in proximity, or to help with the concern of germs when using a public restroom.

Public toilets do not offer clean, sanitary settings for answering the calls of nature. Splatter, spills and accumulated filth coat the toilet and the walls and floors of bathroom stalls. These conditions pose extensive problems for young children particularly, as they lack the balance, dexterity and experience to make use of the facility without touching these soiled areas. Many products require traveling with a large apparatus and cleaning it when at home. Other products, like toilet seat covers, do not ensure a child or adult will not touch filth and germs in public restrooms and serve no purpose when a proper restroom is unavailable.

Similar prior inventions have been described as an aide in toilet training, a toilet surrogate where none is available and a toilet avoidance measure for times when available toilets and stalls have been rendered unsanitary from improper use or inadequate cleaning.

One urinal, Cheng's "V-Cup"[1], is lacking in several important regards.

1—The V-cup has a flat bottom construction such that it cannot be folded down into a compact carrying size. In fact, this device does not appear to be compactible at all. Its size and shape prevent it from being tucked into a pocket, and most gentlemen do not casually carry satchels or briefcases. Fathers on outings with little girls or very young boys could either walk around carrying the V-Cup by hand, leave it in the car (where it may or may not be not readily available), or tote it in some form of pouch. Many women carry purses or day bags, but such accessories may not be large enough, or have the available space with regard to other items already being routinely carried, to stow the V-Cup. Mothers that carry diaper bags for younger siblings not yet potty-trained may have room in these bags, but may nevertheless not appreciate the additional bulk of the rigid V-Cup.

2—The V-Cup's pointed edges on the top slope may cause discomfort when in contact with skin.

3—The V-Cup's method has the user place the device between their legs, hold it in place by squeezing the legs, and steady it with one hand while urinating. This technique could prove problematic for young girls. Young children lack the arm reach and dexterity to securely hold the device in place without bending over. This forward-leaning stance leaves the child balancing precariously and susceptible to sway or fall, resulting in a spill, splash or other messy mishap. Most young children lack the mental focus, motor control, muscle development, coordination and balance to properly perform this task. Even with an assisting parent, keeping the child in a more upright position presents less risk in terms of avoiding spills and falls.

Prior inventions possess complex features and/or sophisticated processes that may increase the cost and present a complicated appearance. These prior inventions may be confusing or intimidating, especially to young children prone to fearing or rejecting unfamiliar objects. A complicated-looking urinal or toilet may intimidate or unsettle the erratic sensitivities of a young child.

Refers to: Sun—US2004/0064112 A1, Wu—US2007/0270716 A1, Cross—US 1993/5243712 A, Sullivan—US1963/3099017, Breece—US1965/3200415.

Prior inventions may involve the use of costly and comparatively bulky absorbent granules, gels or liner materials. These additions in form and function do not necessarily improve the product because they also include real drawbacks, such as added bulk, extra weight and increased costs of production. The absorbent materials provide minimal benefit, in that, in the vast majority of cases, the used receptacle may be discreetly emptied, and therefore rendering the absorbency feature irrelevant. Even in standstill traffic, it would be easy to open the car door and empty the contents onto the ground, without posing health or sanitation risks due to the relative sterility of urine. The situations that might arise where someone would be stuck holding a filled receptacle of urine are so rare as to not justify the added bulk and expense of absorbent materials as a rule.

Refers to: Sun—US2004/0064112 A1, Carter—U.S. Pat. No. 7,996,930 B2, Hills—US2010/0175179 A1.

Prior inventions feature top apertures that do not adjust easily (or at all) in size and/or shape, limiting their versatility and applicability to the broad range of human anatomy. Very small children and those who toilet train very early on, compared to peers, can require a receptacle fit markedly different from the average child. Similarly, heavy-set children with thicker thighs or slender children with thinner thighs will have different fit requirements, with different contact points and pressure, than either the average child or the very small child. Because of this, prior inventions that pop open to a standard/fixed size and form without the ability to easily adjust the top opening wider or narrower can be difficult to use with many children. Adult women of all shapes and sizes will experience the same configuration divergence, diminishing the suitability of a standard, non-adjustable device.

Refers to: Cheng—US2008/0034481 A1, Sun—US2004/0064112 A1, Cross—US1993/5243712 A, Breece—US1965/3200415.

Prior inventions present heavier, bulkier alternatives that greatly reduce their portability and stowability. Some are so bulky and heavy that they would require special accommodations for carrying. There are many occasions where gentlemen travel with little more than car keys, and women (alone or with children) carry only small- to medium-sized purses. The inability of many of the prior inventions to stow neatly, quickly and unobtrusively in a pants pocket, small purse, or glove box is antithetical to the on-the-go, modern lifestyle.

Refers to: Sun—US2004/0064112 A1, Carter—U.S. Pat. No. 7,996,930 B2, Hills—US2010/0175179 A1, Thomas—US2008/7334273 B2, Gara—US2006/0150312 A1, Aguila—US2012/8117681 B2.

Prior inventions make use of a soft bag of some sort as the urine containment receptacle. The urine collects at a relatively vertical drop, placing the containment bag between the legs of impatient, wriggling toddlers. The slightest bump could push the side(s) of the bag in, having no stronger supporting structure around it, and slosh any urine not yet absorbed by the liner in a fountain. Even older children can have a difficult time standing completely still. More, devices that collect in a vertical-drop fashion to a receptacle positioned between the legs, regardless of the strength of the receptacle puts the collected urine directly between, and in too close proximity to, the very things the receptacle should avoid contact with: children's legs. Collection away from the body would be a preferable alternative. Even adults are susceptible to this kind of accident, particularly if using the urine receptacle in transit (e.g.—plane, train or bus) where jostling during urination is likely. Air turbulence in flight could cause a sudden lurch to the side, where both legs meet in the middle, crushing the receptacle and hurling the fluid out the top.

Refers to: Cheng—US2008/0034481 A1, Hills—US2010/0175179 A1.

Prior inventions do have collapsing, folding and stowing features, yet manage to remain still bulky, weighty, and expensive. They additionally do not lend themselves to a speedy or clean process. Any device requiring the user to sit, or squat over a receptacle, held or placed on the floor, could result in lower body clothing to be lowered nearly to the ankles, where it can then come into contact with dirty floors. Positioning the body and maintaining a balanced posture over a small surrogate toilet or urinal, while keeping clothes away from dirty surfaces, requires more time and effort than other methods. An inquisitive, inattentive child further compounds this problem, as they are suddenly in position and within hand's reach of the dirty floor. Additionally, neither adults nor children may use such squatting or seating devices discreetly They must find a place away from trafficked areas where toilet use does not garner personal embarrassment or outward offense.

Refers to: Carter—U.S. Pat. No. 7,996,930 B2, Gara—US2006/0150312 A1, Bailey—US2000/6047414 A, Thomas—US2008/7334273 B2.

Prior inventions offer neither compact size nor disposability, making them burdensome to carry and maintain. These devices cannot be unobtrusively carried, nor disposed of after use, and must be cleaned before using again. These labor-intensive methods do not conform with today's fast-paced, on-the-go, modern lifestyle. Additionally, what cost savings may be realized by using a non-disposable item over a multitude of disposable ones, may come with greater costs incurred in convenience lost, time lost and additional effort expended to use and maintain.

Refers to: Thomas—US2008/7334273 B2, Myers—US2008/7363661 B1.

Numerous prior inventions designed to aid or enable female urination feature one or more of the following characteristics: lightweight, foldable, portable, stowable, disposable, discreet, and affordable. However, these prior inventions function as funnel-type conduits for urine, rather than capture/collection devices, and serve no purpose for solid excrement or vomit. This shortcoming poses several problems for small females. First, some toilet-trained young girls remain too short in stature to use a funnel-conduit with a public toilet because the edge of the toilet stands taller than the outer, lower end of the conduit. The child would have to stand on the seat or be suspended over it in the arms of the parent, while attempting to simultaneously hold the device in place, remain steady and accurately direct the flow of urine. If the user cannot stand slightly above and over the toilet basin edge, proper usage becomes difficult. Second, even taller children and adults must position themselves very near the filthy toilet, thereby becoming susceptible to inadvertent brushing of hands or forearms against unsanitary surfaces. Third, in both the aforementioned first and second regards, the user would lower or remove clothing to properly use the device, increasing the exposure of bare skin and outer clothes to the unsanitary surfaces. Even an adult female must get close enough to the toilet that she risks brushing her lower clothing against the toilet seat or bowl.

Fourth, use of these prior inventions requires that the user be standing over a toilet, or outdoors in a location where the urine flow draining to the ground is of no consequence. With young girls, bladder awareness and control may not be fully developed. These young girls may have sudden, immediate urges to relieve themselves while lacking the control to wait for a suitable time and place to do so. This urgency places a tremendous amount of stress on the child, at the same time panicking the parent that seeks to avoid "an accident." In the times these emergency calls of nature occur in a car, or other locales where urination can be impossible, uncouth, or dangerous, the conduit device would be of no use without some kind of additional container available to collect the draining urine. Lastly, adult women also receive additional benefit from the present invention over prior inventions, for the same reasons stated in the fourth aforementioned regard. Women occasionally need to relieve themselves while far away from a toilet or suitable outdoor ground. Moreover, women contending with mild incontinence might be at such a distance away that they cannot reach the restroom or suitable ground in time to use the funnel-conduit device.

Refers to: Filsouf—US2002/6434757 B1, Montakhabi—US2010/7694819 B2, Oprandi—US2012/8221367 B2, Mottale—US2002/6460200 B1, Cross—US1993/5243712 A, Cicio—US1995/5408703 A, Cicio—US1998/5742948, Rudolph—US2009/0089919 A1.

A young girl on an all-day outing with her mother might need to use the restroom several times, in addition to any restroom visits the mother would require for herself. A mother of two girls and a young boy could easily have upwards of twenty-five restroom visits away from home in a single month. The costs of disposable items can add up quickly, making affordability an important aspect of disposable urine receptacles; however, it doesn't automatically follow that disposable receptacles should sacrifice minimum levels of performance to achieve affordability. Foldable, disposable receptacles that appear to be very affordably produced may nevertheless suffer inferior levels of performance in other important areas. An affordable disposable device should offer simultaneous, satisfactory performance in ease and speed of use, convenience, ergonomics, size, and utility across a variety of locations or situations. Any prior inventions not meeting these key performance parameters while maintaining affordability may not provide suitable benefit.

Refers to: Wook-Joong Shin—US2006/7086097 B2, Aguila—US2012/8117681 B2, Mottale—US2002/6460200 B1.

SUMMARY OF INVENTION

Embodiments herein can provide a foldable, lightweight urine receptacle that is compact, easily stowed, sanitary and disposable and can be used by children or adults when there are no restrooms available or the restrooms are unsanitary. This device is not limited to the capture of urine alone as it can hold all forms of excreta.

The receptacle can be folded into a lightweight, compact size, making it easily portable and easily stowed in small spaces (e.g.—in a pocket of adult clothing, a handbag or automobile glove box). The receptacle can be folded in half or thirds. Its bi- or tri-folded size can be comparable in bulk and weight to a common, economy No. 10 business envelope with one or two sheets of standard, 20 lb, legal-size, copy paper enclosed and similarly bi- or tri-folded. Its compact size can ensure provision of a situation for the child or adult to urinate when there are no restrooms in the vicinity. Compact sizing can increase the likelihood of finding a place for stowing one or more receptacles to bring along on outings. The receptacle's familiar shape (similar to that of a tall cup or paper envelope) can alleviate the intimidation new users or children might feel when the device is introduced for use.

The urine receptacle disclosed herein can make restroom encumbrances much easier with children. It can make it possible for a child to avoid manual or casual contact with contaminants while in a public restroom. The child (or adult) can walk in, urinate, and walk out without having handled anything in the restroom. In further example, it facilitates public restroom use with very young boys. Very young, early toilet-trained boys, who are too short to stand in front of the toilet/urinal and urinate into the basin, can urinate into the receptacle with the aid of an adult, and alone with time and practice. This urine receptacle mitigates the problem of little boys leaning up against the front of a public toilet when trying to urinate or having to attempt to urinate while being suspended above the toilet/urinal by a parent. It can also reduce the amount of time needed to take a child to the restroom, regardless of location. Using the receptacle can circumvent the common procedures for taking a child to the restroom (eg—find a restroom, remove lower clothing, prepare the toilet for contact with the child with barrier or cleaning devices, keep the child from the dirty surfaces while grabbing for toilet paper, put the clothes back on, wash the child's hands or legs after contact with dirty surfaces, etc. . . . ) and can potentially cut the time needed to complete the task by half or better. It may also similarly speed up the process for adults.

The receptacle can be held with one hand for use by adults assisting children, or independent one-handed capture by adults or children of appropriate age. Given time and practice it is possible for the child to learn to use the receptacle independent of adult assistance leading to a greater sense of accomplishment and autonomy in the child. The urine can be captured in a downward, diagonal angle which directs the urine away from the body and can enable children to use the device independent of an assisting adult because they can stand more upright and can maintain a more balanced stance than with a urine receptacle that collects in a downward direction between the legs and, causing them to bend forward. The one-handed capture can be an aid to parents with certain physical limitations or disabilities, who might otherwise find difficulty in taking their children to public restrooms.

When finished urinating, the taller end of the receptacle can be drawn forward in a squeegee-like manner, effectively sweeping any drops or residue into the receptacle, eliminating the need for toilet tissue and wiping. If needed, the receptacle can stand alone on a reasonably flat surface, in a variety of embodiments, while containing urine. This can permit the user to set the used device aside in order to first complete tasks of a higher priority, before disposing of the contents of the receptacle.

It can be removed from a lightweight, protective wrapper, where the receptacle is kept clean until it is ready to use, and can be folded back down into its original compact shape, and replaced back into the thin protective wrapper to prevent leaking of residual urine from the receptacle. Without a protective wrapper, keeping the device clean prior to first use could be challenging. The device can be kept in purses, bags, glove boxes, etc., all of which could soil the receptacle if it was not otherwise wrapped.

The top aperture can easily and quickly be made wider or narrower, in pursuit of a comfortable fit, by applying pressure or relaxing the grip while in hand, in order to accommodate the anatomy of the person. To widen the opening, the user merely squeezes the body of the device, causing the two sidewalls to bow outwards. Conversely, by slightly relaxing the grip, the two sidewalls of the receptacle retract in on each other (towards each other and the original flat configuration), making a narrower opening. Adjusting the variable top aperture to more closely reflect the shape of the groin area can provide a more comfortable, functional fit. A more accommodating fit can also mean less chance of spills, backflow, sloshing or fountaining of the urine flow during use.

While many of the other prior inventions above could achieve one or more of the benefits described herein, they may be unable to provide the same simultaneous levels of ease of use, speed of use, variety of location of use, convenience of use and affordability as this present invention in its various embodiments.

BRIEF DESCRIPTION OF DRAWINGS

FIG. 1 Front view of receptacle 100 in an open, usable configuration
FIG. 2 Back view of receptacle 100 in an open, usable configuration
FIG. 3 Side view of receptacle 100 in a flat configuration
FIG. 4 Back/bottom perspective view of receptacle 100
FIG. 5 Side View of receptacle 100A with bag-like liner
FIG. 6 Back/bottom perspective view of receptacle 100A with bag-like liner
FIG. 7 Front view of receptacle 200 in an open, usable configuration
FIG. 8 Back view of receptacle 200 in an open, usable configuration
FIG. 9 Side view of receptacle 200 in a flat configuration
FIG. 10 Side/bottom perspective view of receptacle 200 in a mostly flat configuration
FIG. 11 Front view of receptacle 200A showing bag-like liner over rolled edge top
FIG. 12 Back view of receptacle 200A showing bag-like liner over rolled edge top
FIG. 13 Front view of receptacle 200B showing bag-like liner rolled together with base material to make rolled edge
FIG. 14 Back view of receptacle 200B showing bag-like liner rolled together with base material to make rolled edge
FIG. 15 Front view of receptacle 300 in an open, usable configuration
FIG. 16 Back view of receptacle 300 in an open, usable configuration
FIG. 17 Side view of receptacle 300 in a flat configuration
FIG. 18 Side/bottom perspective view of receptacle 300 in a mostly flat configuration
FIG. 19 View of receptacle in use with a child
FIG. 20 Top view of tri-folded receptacle in a flat configuration
FIG. 21 Top/side perspective view of tri-folded receptacle in a mostly flat configuration
FIG. 22 Top/side perspective view of bi-folded receptacle in a flat configuration
FIG. 23 Top view of tri-folded receptacle in a flat configuration
FIG. 24 Top view of closed/sealed envelope with adhesive strip closure
FIG. 25 Back view of open, re-sealable envelope with flat, tri-folded receptacle inserted

DESCRIPTION OF EMBODIMENTS

FIG. 1, FIG. 7 and FIG. 15 depict disposable, foldable urination receptacles 100, 200 and 300, respectively, each in accordance with one potential embodiment. The receptacles 100, 200 and 300 serve as collection and containment devices used for children and adults and can facilitate urination in a standing or seated position for both males and females. The receptacles 100, 200 and 300 can be a single piece, folded into design, wherein the base material can be cardboard, firm, compressed paper, lightweight plastic or other flexible, manufactured material. Other materials and combinations of materials can be utilized, as would be obvious to those skilled in the art. In other embodiments the base material can be made from recyclable materials and green energy by-products.

The receptacles 100, 200 and 300, in all potential embodiments, can be saturated, or otherwise endowed, with a liquid-resistant or liquidproof coating or layer, or made from liquid-resistant or liquidproof materials and/or composite paper, thereon its interior and/or exterior. This provides for a liquid-resistant or liquidproof container that, by way of the curved contour 104, can be placed flush against, or in close proximity to the source of urination. The curved contour 104 can provide for a comfortable fitting and structural fit. In other embodiments the materials can be made from recyclable materials and green energy by-products.

Figures 11, 12:
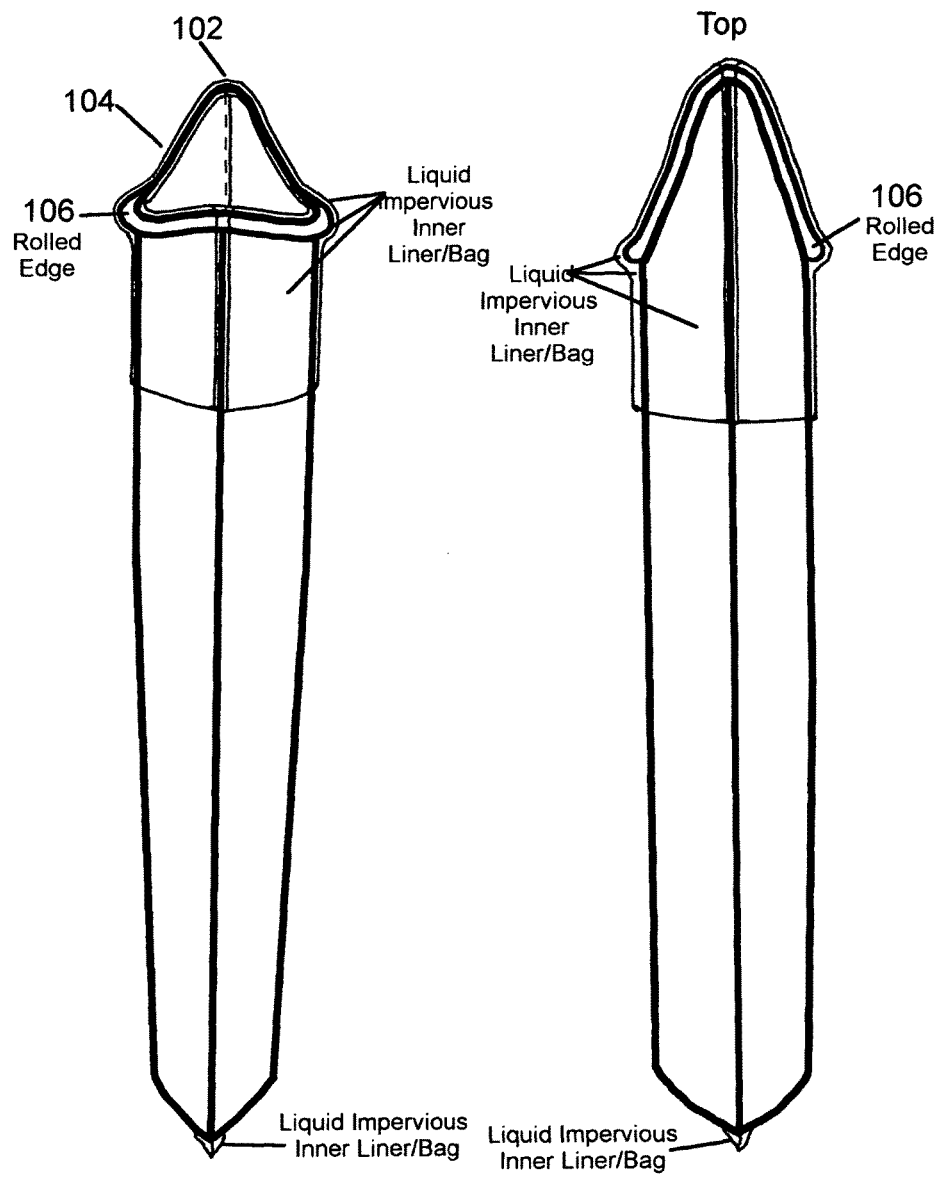

As shown in FIG. 1, the top of receptacle 100 can consist of a rolled edge 106 to provide comfort and structural support. The rolled edge 106 can be a rolling of the base material and may include a rubber, adhesive lining, or other manner of temporary or permanent sealing material and method as would be obvious to those skilled in the art, for sealing purposes against the body during use, and/or also upon closure, to prevent urine from leaking after use. This preferred rolled edge feature may allow the device to be accommodating and safe whenever there is contact with the body or skin. As shown in FIG. 5, FIG. 7 and FIG. 15, the interior liquid-resistant or liquidproof material can extend up over and fold back down upon the top exterior of the receptacle in a form-fitting or loose-fitting manner, and can be adhered, or in other ways obvious to those skilled in the art attached, fastened and/or joined, to the interior, exterior or to itself, in full or in part; in this or other such embodiments, the liquid-resistant or liquidproof material can be a plastic bag or similar flexible, manufactured material that can cover over the top aperture edge to provide a comfortable fit, covering sharp edges, and avoiding paper cuts or other abrasions. As also shown, the liquid-resistant or liquidproof material can extend up over the top and fold back down upon a top opening that is a rolled edge (FIG. 5), that is not rolled edge (FIGS. 7 & 15), or that is an edge with different possible treatments obvious to those with ordinary skill in the art. As shown in FIG. 11 and FIG. 13, the liquid-resistant or liquidproof material can extend up over and back down upon the top exterior of the receptacle like a short sheath (FIG. 11) or can be rolled in with the base material (FIG. 13), or as part of the base material (FIG. 13), into the rolled edge and not extending down the exterior of the top of the receptacle like a short sheath. This feature, the covering over of the top edge with the inner liquid-resistant or liquidproof material, either by extension, additional material and joining or fusing methods, and other methods obvious to those of ordinary skill in the art, may allow the device to be accommodating and safe whenever there is contact with their body or skin.

Figures 3, 4:
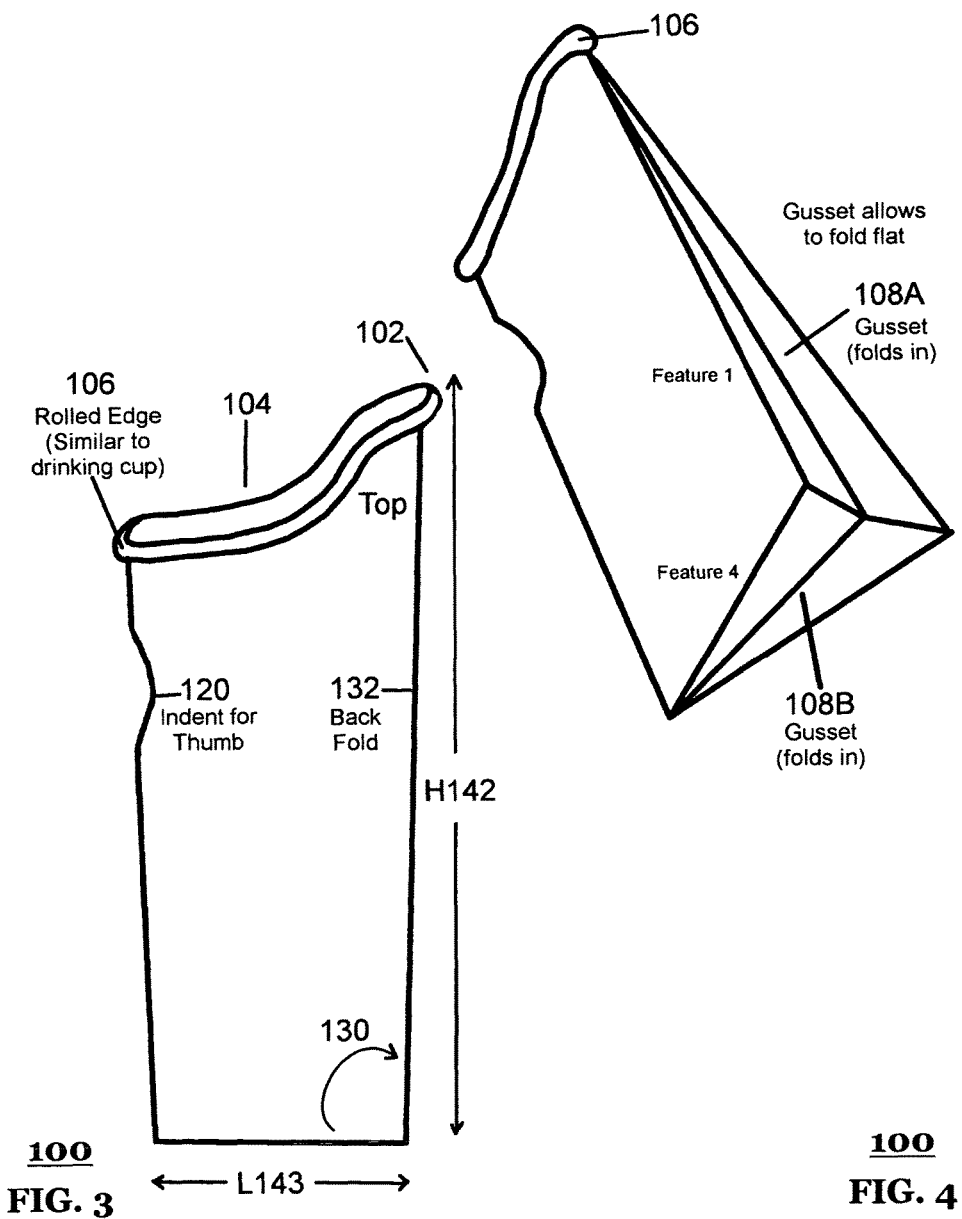

In FIG. 4 of receptacle 100, the gussets shown, Feature 1 (lateral, 108A) and Feature 4 (posterior, 108B), may allow the device to fold inward and flat, making it easy to handle, stow or store. In FIG. 6, the area of material that forms the posterior/bottom gusset 108B, can be removed to allow for a hollow bottom and a bag-like, liquid-resistant or liquidproof material lining to be revealed, while yet allowing the device to fold inward and flat, making it easy to handle, stow or store. Feature 6 on FIG. 6 depicts the posterior gusset 108B removed and having an open bottom configuration. When both gussets remain (FIG. 4), the interior liquid-resistant or liquidproof materials liner can be bag-like or other non-bag like, liquid-resistant or liquidproof materials and methods. The embodiments in receptacle 200 (FIGS. 7 & 10) and receptacle 300 (FIGS. 15 & 18), show the gusseted edges can be replaced by folds, as well as having a hollow bottom structure (no firm bottom, or no bottom other than an interior bag-like liquid-resistant or liquidproof material). In other words, the single piece, folded into design, can be open at the top and open at the bottom (tube-like), allowing the device to fold inward flat making it easy to handle, stow or store, in conjunction with a bag-like, interior liquid-resistant or liquidproof material. The receptacle embodiments can be free-standing, whether empty or full, with a firm bottom or without a firm bottom, and/or with two or more gussets, only one gusset, or no gussets.

The receptacle 100 (FIG. 1) can permit for one-handed use by an adult, offered by the preferred feature of a thumb indent 120, in order to free the remaining hand to steady oneself or a child when seated or standing, hold toilet paper at the ready, or fulfill similar common needs. Feature 120 is the indentation intended for the thumb of the person using the device with a child and can be positioned in the general area illustrated in FIG. 1, but is not limited to this location, nor are potential notches or similar indentations limited to thumbs. This subtle notch is an improvement in grip and aids in the prevention of slippage. The thumb indent can be manifested by a folding of the base material from manual depression or other means obvious to those skilled in the art. The receptacles 200 and 300, FIG. 7 and FIG. 15 respectively, do not show a thumb indent, but this is not meant to indicate that a thumb indent is undesirable. While a thumb indent is a preferred feature, it can be omitted from inclusion in an embodiment without significant adverse consequences in performance. The receptacles 100, 200 and 300, in all potential embodiments, provide for independent, unsupervised use by a child, after a certain age and/or duration of practice. Receptacles can be used in public restrooms, cars, and anywhere else a restroom is unavailable or unsanitary.

Figures 17, 18:
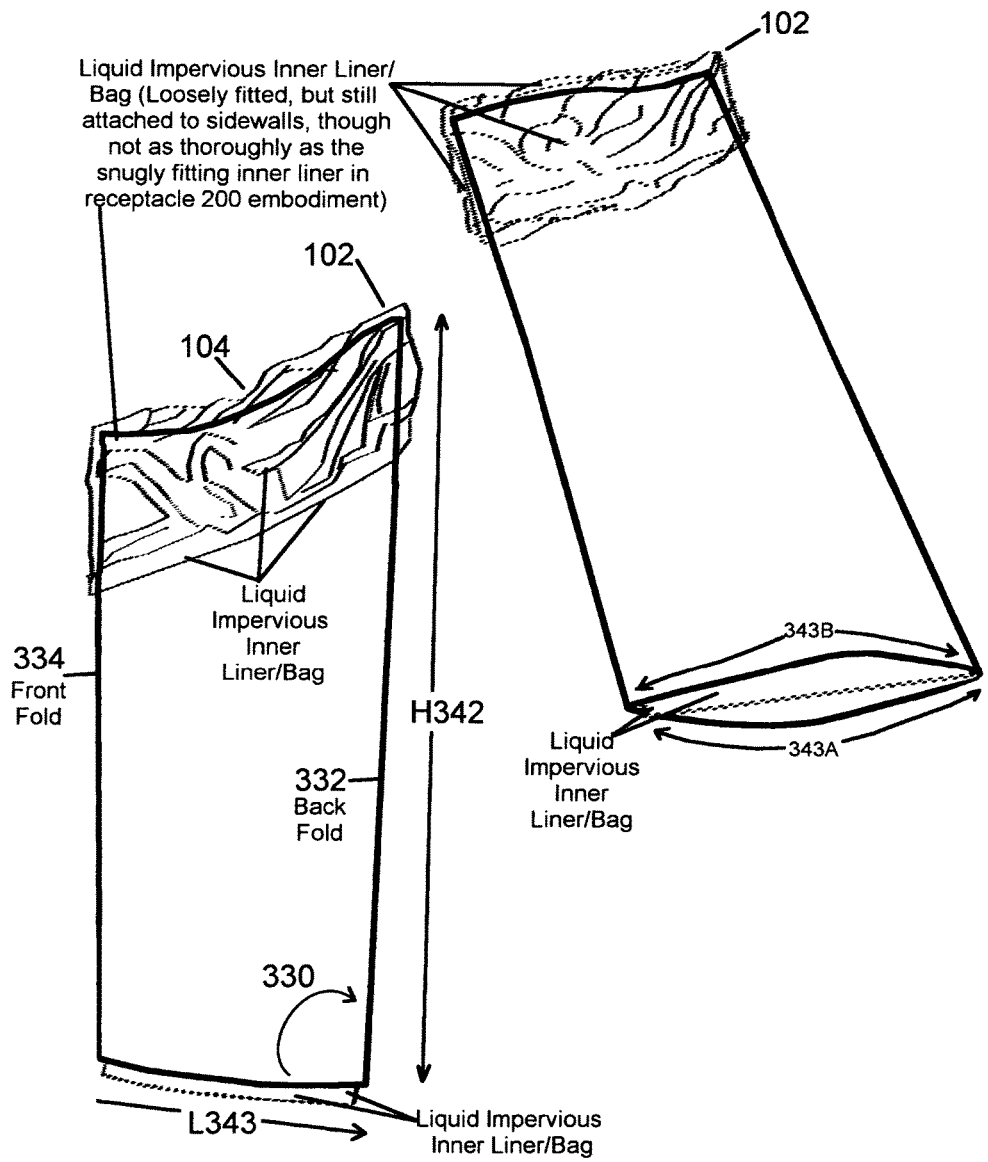
Figure 19:
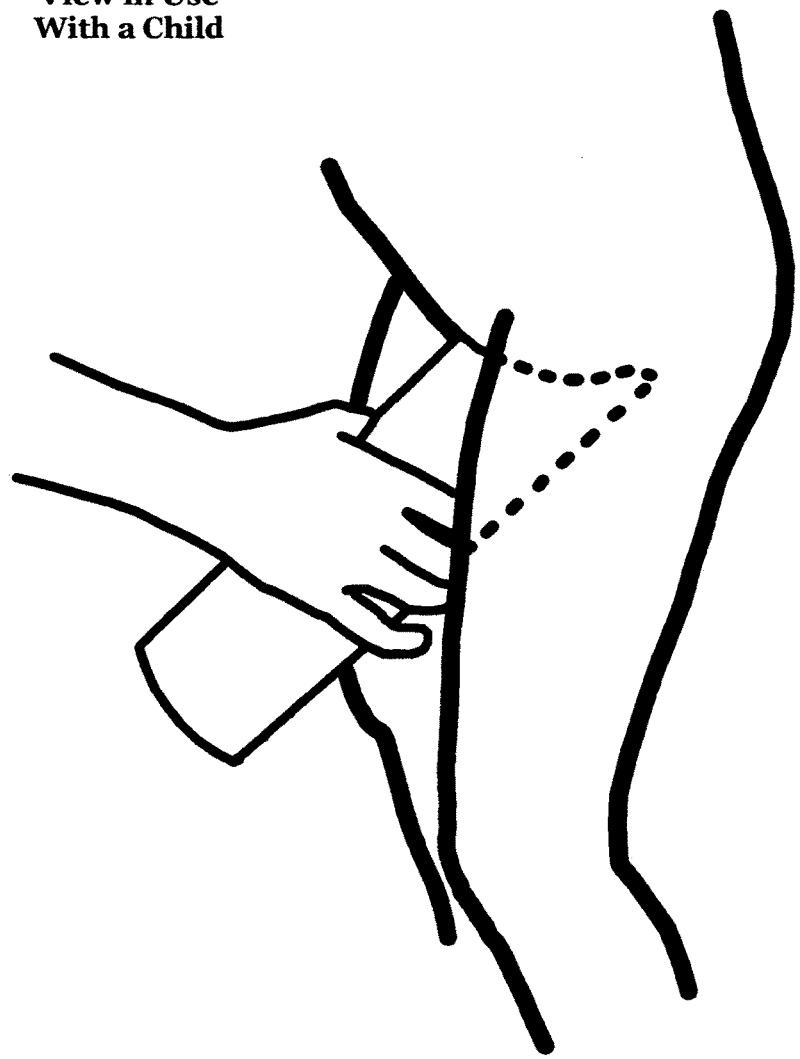
Figure 20:
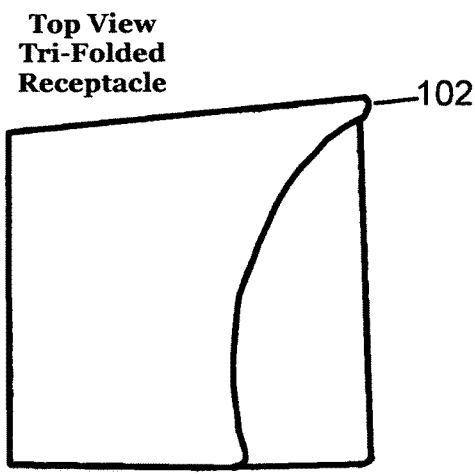

FIG. 3, FIG. 9 and FIG. 17 illustrate side views of the receptacles 100, 200 and 300, respectively, showing the saddle-shaped and uniquely asymmetric and sloping curvature of the topside opening that can be attributed to the curved contour 104 feature. This device can be held for use at approximately a 45 degree angle (FIG. 19). The angle of the top can make the invention fit and seal against the skin (FIG. 19) to avoid leaks, backsplash and overflow. As noted in FIG. 3, this angled inclination 130 can be derived due to its utility in an approximately 45 degree angled orientation and facilitates a downward diagonal capture. The angled inclinations 130 (FIG. 3), 230 (FIG. 9), and 330 (FIG. 17) of the back fold corners 132, 232, and 332, respectively, may direct the urine flow, and collection thereof, away from the body in a downward diagonal direction according to the respective angled inclination 130, 230 or 330, as indicated. In one embodiment, the angle can be between 100 and 120 degrees. In other embodiments, the angle can be between 80 and 100 degrees. Other angles are possible in other embodiments. The angles of the front fold corners 134, 234 and 334 of receptacles 100 (FIG. 3), 200 (FIG. 9) and 300 (FIG. 17), respectively, can vary according to the angled inclination of the back fold corners of the device.

As also shown in FIG. 3, FIG. 9 and FIG. 17, the unique curvature captured by the curved contour 104 of the top opening, rises higher towards the back and/or gusseted lateral side, 132, 232 and 332 respectively, in order to prevent backflow of the urine stream onto the child or clothing. It also can be designed with a curve (for example, but not limited, to −10 to 30 degrees in one embodiment) that, with slight pressure, be wiped forward (away from the buttocks) on the genitals of a female, removing urine droplets or residual urine (similar to the function of a squeegee), and alleviating the need for toilet paper where none is readily available.

In FIG. 1 and FIG. 3 of receptacle 100, the two sides 143A and 143B can create the back fold corner 132 and front fold corner 134. In FIGS. 7 & 8 of receptacle 200, the two sides 243A and 243B can create the back fold corner 232 and the front fold corner 234. In FIGS. 15 & 16 of receptacle 300, the two sides 343A and 343B can create the back fold corner 332 and front fold corner 334. As shown in FIG. 3, FIG. 9 and FIG. 17, the height 142, 242 or 342 of the example embodiment receptacles can be between 4-13 inches. The length of the sides 143, 243 or 343 that can create the back fold corners 132, 232 and 332 respectively, can be between 2-9 inches. Other lengths are possible in other embodiments. The back corners 132, 232 and 332 can be created from the folding of the sides. The gusset 108A (FIG. 2) can be between 2-9 inches in length. This folding of the sides can also create the positioning peak 102 (FIGS. 3, 9 & 17) which provides for secure and comfortable placement during use. The symmetry of the positioning peak 102 feature can provide to the holder, a measure of indication that the receptacle 100 is properly positioned on females, for example, from mid-line just above the urogenital cleft to just past the beginning of the buttocks.

FIG. 4 presents a perspective back view of the disposable, foldable urination receptacle 100. In this illustration, the gussets 108A and 108B can allow for the receptacle 100 to fold flat. The gussets are initially folded flat and can be manually opened to expand the interior volume of the receptacle 100 to receive urine. Features 1 (108A) and 4 (108B) show that the lateral gussets can collapse, laying the sidewalls flush against each other and flattening the device. FIG. 10 and FIG. 18, of receptacles 200 and 300 respectively, present a perspective side/bottom view of other potential embodiments of the foldable, disposable urine receptacle. The sidewalls 243A/B and 343A/B can also be initially folded flat and can be manually opened to expand the interior volume of the receptacles 200 and 300, respectively, to receive urine. In the embodiments where an interior liquid-resistant or liquidproof material resembles a plastic bag in form and function, for instance FIGS. 6, 10 and 18, the interior liquid-resistant or liquidproof materials can be manually opened simultaneously with the sidewalls.

FIG. 19 illustrates the distinctly angled approach of a receptacle intended for use with a child. The receptacle 100, 200 or 300 can be positioned at an approximately 45 degree angle to the body between the child's legs to allow urination. This angled position may allow the child to minimally spread their legs, draws the stream of urine away from the body, and does not require fully removing any garments in the process. Manually squeezing the lateral sides, 132/134, 232/234, or 332/334, of the device towards each other can flexibly adjust the length and width of the opening. The rigid yet flexible base material (e.g., cardstock, recycled cardboard, composite paper, etc.) may permit for conditions where the greater the pressure applied to the lateral sides, the larger the width and shorter the length of the opening become in proportion to the unique stance of any child at any given time, regardless of garment or other restrictions on positioning of the legs and feet. This design, requiring light and continuous pressure to maintain the opening shape, can also permit the continuous, flexible adjusting of the opening shape and fit during the course of urination if the child starts wiggling, fidgeting or in some manner disrupting the initial fit of the device.

Figure 21:
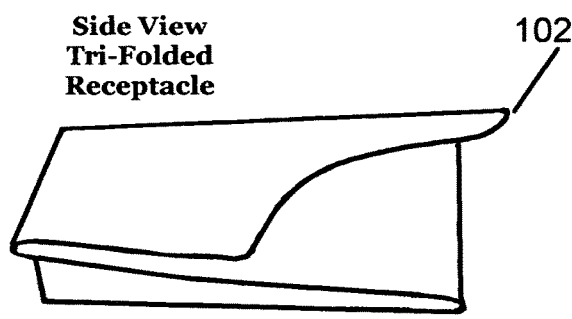
Figure 22:
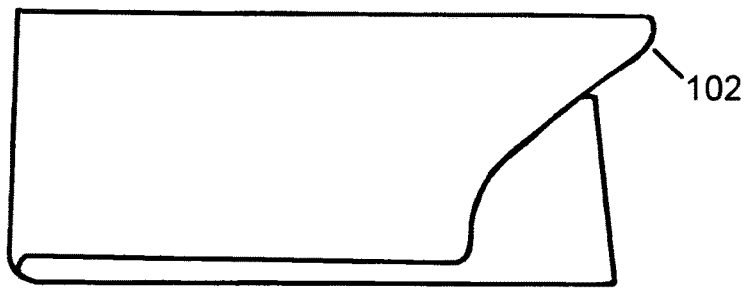

These embodiments of the receptacles disclosed herein can be folded flat, and then bi-folded (FIG. 21) or tri-folded (FIG. 22) to configure into a size able to fit quickly and easily into an adult pocket. These receptacles can be individually wrapped (FIG. 25) (eg—cellophane pouch, transparent envelope, poly/plastic type disposable container, or other lightweight sealable and/or re-sealable container as would be obvious to those skilled in the art) to make it easy and compact to store in cars, purses, pockets, etc. Its utility as a sanitary and portable apparatus derives from its construction to fold flat and in a size that is compact. This makes it easy to stow or store multiple receptacles and always have them on hand.

The urine receptacles are not limited to the uses described above. They can function as a multi-purpose liquid receptacle, waste or excreta receptacle, vomit receptacle and temporary container as separately required.

Upon reviewing the aforementioned embodiments, it would be evident to an artisan with ordinary skill in the art that said embodiments can be modified, reduced, or enhanced without departing from the scope and spirit of the claims described below. Accordingly, the reader is directed to the claims section for a fuller understanding of the breadth and scope of the present disclosure.

While the invention has been described in conjunction with specific embodiments, it is evident that many alternatives, modifications, permutations and variations will become apparent to those of ordinary skill in the art in light of the foregoing description. Accordingly, it is intended that the embodiments of the present invention embrace all such alternatives, modifications, permutations, advancements and variations as fall within the scope of the appended claims. While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

CITATION LIST

| EI* | Document Number | Publication Date | Patentee | Paragraph No.: Line No. |
|---|---|---|---|---|
| R C | 7,996,926 B2 | Aug. 16, 2011 | Aguila, Wilfred | |
| R C | 8,117,681 B2 | Feb. 21, 2012 | Aguila, Wilfred | |
| R C | 8,209,786 B2 | Jul. 03, 2012 | Aguila, Wilfred | |
| C E P | 6,047,414 | Apr. 11, 2000 | Bailey, Gerald | |
| L J L | 3,200,415 | Mar. 01, 1963 | Breece, Jr., L. K. | |

-continued

| EI* | Document Number | Publication Date | Patentee | Paragraph No.: Line No. |
|---|---|---|---|---|
| R J C | 7,996930 B2 | Aug. 16, 2011 | Carter, William | |
| — | 2008/0034481 A1 | Feb. 14, 2008 | Cheng, Bernard | [FIG. 1B], [0045: 22, 31, 38] |
| C E P | 5,408,703 | Apr. 25, 1995 | Cicio, William | |
| C E P | 5,742,948 | Apr. 28, 1998 | Cicio, William H. | |
| H J R | 5,243,712 | Sep. 14, 1993 | Cross, Leta K. | |
| G H | 6,434,757 B1 | Aug. 20, 2002 | Filsouf, Ehsan | |
| — | 2006/0150312 A1 | Jul. 13, 2006 | Gara, Peter | |
| — | 2010/0175179 A1 | Jul. 15, 2010 | Hills, Robin Gray | |
| B P G | 7,694,819 B2 | Apr. 13, 2010 | Montakhabi, Saeid | |
| D J W | 6,460,200 | Oct. 08, 2002 | Mottale, Sima | |
| C E P | 7,363,661 B1 | Apr. 29, 2008 | Myers, Stanley Ann | |
| T Z | 8,221,367 | Jul. 17, 2012 | Oprandi, Arthur V. | |
| — | 2009/0089919 A1 | Apr. 09, 2009 | Rudolph, Cynthia K. | |
| — | 3,099,017 | Jul. 30, 1963 | Sullivan, L. J. | |
| — | 2004/0064112 A1 | Apr. 01, 2004 | Sun, Robert | |
| C E P | 7,334,273 B2 | Feb. 26, 2008 | Thomas, Annie L. | |
| H L | 7,0886,097 B2 | Aug. 08, 2006 | Shin, Wook-Joong | |
| — | 2007/0270716 A1 | Nov. 22, 2007 | Wu, Chen Hung | |

*Examiner's Initials (where available)

The invention claimed is:

1. A disposable receptacle comprising:
   a panel of continuous material defining an enclosure and having an inner surface and an outer surface; and
   wherein the receptacle has a first mode in which the material is folded along a fold line into a lay flat position and a second mode in which the receptacle is expanded outwardly relative to the fold line to form a volume in the enclosure,
   wherein when the receptacle is in the second mode:
      an asymmetric, curved contour opening at a top end of said receptacle is formed, wherein the curved contour opening defines a peak at one end of the opening,
      a bottom for containing liquid disposed therein is formed, the bottom being opposingly spaced-apart from the top and defining a base surface facing outward of the receptacle for positioning the receptacle about a support surface,
      wherein the fold line extends from the bottom to the peak of the opening,
      wherein the length and width of said opening is variably adjustable by a user applying varying amounts of pressure with his or her hand directly around said outer surface of said receptacle.

2. The receptacle of claim 1, wherein said opening is configured to conform to and enclose a person's genital area.

3. The receptacle of claim 1, further including a coating on the receptacle, wherein said coating or layer is selected from the group consisting of a wax coating applied to said inner surface, a liquid-resistant liner, and a polyethylene coating applied to said inner surface.

4. The receptacle of claim 1, wherein said opening comprises a nonabrasive rim.

5. The receptacle of claim 1, wherein the receptacle is free-standing.

6. The receptacle of claim 1, wherein said outer surface is one of cardboard, compressed paper, and plastic.

7. A disposable receptacle comprising:
   a panel of continuous material defining an enclosure and having an inner surface and an outer surface;
   wherein the receptacle has a first mode in which the material is folded along a first fold line into a lay flat position and a second mode in which the receptacle is expanded outwardly relative to the fold line to form a volume in the enclosure,
   wherein when the receptacle is in the second mode:
      an asymmetric, curved contour opening at a top end of said receptacle is formed, wherein the curved contour opening defines a peak at one end of the opening,
      a bottom for containing liquid disposed therein is formed, the bottom being opposingly spaced-apart from the top and defining a base surface facing outward of the receptacle for positioning the receptacle about a support surface,
   wherein the first fold line extends from the bottom to the peak of the opening, wherein the first fold line is positioned medially between a pair of longitudinally extending fold lines, the first fold line and the pair of longitudinally extending fold lines cooperating to define a portion of the panel of continuous material that is recessed relative to an outer periphery of the receptacle when in the first mode,
   wherein the length and width of said opening is variably adjustable by a user applying varying amounts of pressure with his or her hand directly around said outer surface of said receptacle.

* * * * *